(12) United States Patent
Montgomery

(10) Patent No.: US 6,210,161 B1
(45) Date of Patent: Apr. 3, 2001

(54) BREAKDOWN DENTAL FORCEPS

(76) Inventor: Joseph William Montgomery, 294 S. Shore Dr., Mina, SD (US) 57462

( * ) Notice: Subject to any disclaimer, the term of this patent is extended or adjusted under 35 U.S.C. 154(b) by 0 days.

(21) Appl. No.: 09/444,757

(22) Filed: Nov. 22, 1999

(51) Int. Cl.$^7$ ................................................. A61C 3/14
(52) U.S. Cl. ............................................ 433/146; 433/159
(58) Field of Search .................................. 433/146, 142, 433/159

(56) References Cited

U.S. PATENT DOCUMENTS

| | | | | |
|---|---|---|---|---|
| 733,114 | * | 7/1903 | Anderson | 433/146 |
| 1,376,005 | * | 4/1921 | Cohane | 433/146 |
| 1,518,021 | * | 12/1924 | Truxillo | 433/159 |
| 2,030,798 | * | 2/1936 | Krajeski | 433/159 |
| 5,122,058 | * | 6/1992 | Lukase et al. | 433/159 |

* cited by examiner

Primary Examiner—Todd E. Manahan
(74) Attorney, Agent, or Firm—Curtis V. Harr

(57) ABSTRACT

A breakdown dental forceps is provided in which the jaws are specifically designed to terminate in a flat and fine point which is capable of reaching down into extremely tight places which other dental forceps are unable to enter. The inner edges of the two jaws are also constructed to produce a concave surface on each which allows the jaws to firmly grasp irregularly shaped objects such as the mandibular molar roots. The finely tapered jaws and their concave inner surfaces allow the forceps to be used to grasp the mesial and distal surfaces of a molar which provide more gripping area and results in an easier extraction of the target molar. Additionally, the breakdown forceps is also designed in a manner that allows it to be taken apart which allows for the use of the lower handle and outer jaw or upper handle and inner jaw as a pry instrument used to loosen the mesial and distal roots of a sectioned molar which makes the extraction of those roots from the mandible significantly easier.

18 Claims, 2 Drawing Sheets

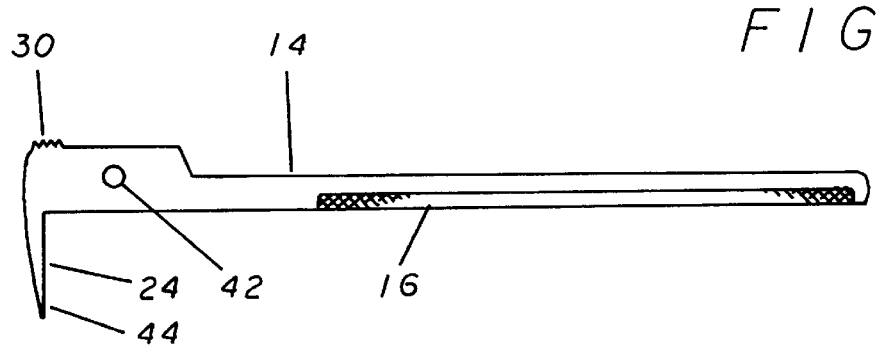
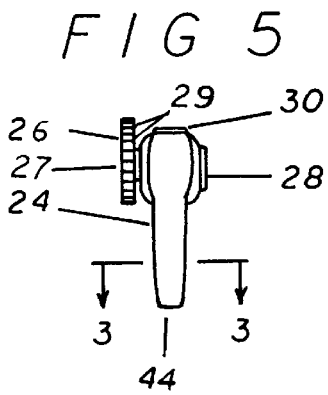
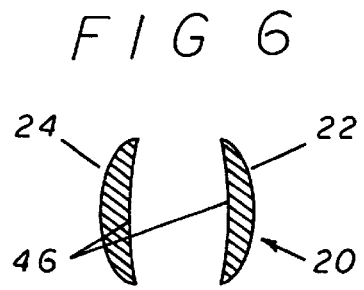
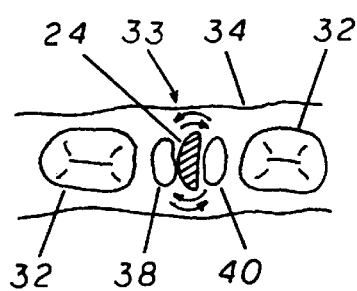
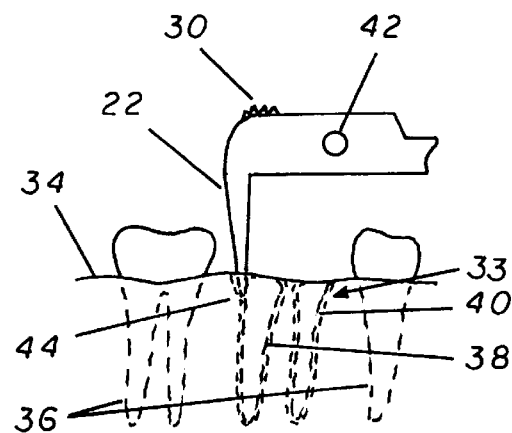

BREAKDOWN DENTAL FORCEPS

BACKGROUND OF THE INVENTION:

The present invention relates to an improvement in the design of dental forceps that are commonly employed in the extraction of molars from the mandible of dental patients.

In the practice of dentistry, it is often necessary to remove teeth for a variety of reasons including extensive decay, fractures or advanced periodontal disease. Teeth with more than one root, such as molars, often require the tooth to be sectioned prior to extraction. The sectioning process entails using a dental hand piece to divide the remaining coronal portion of the tooth into sections so that each root may be removed as an individual unit with any remaining coronal portion of the tooth. Use of the currently available instruments often results in forces being applied to the root during extraction that may lead to fracture of the root tip below the level of bone which leaves portions of the root inaccessible to the operator thus, requiring a surgical procedure in order to gain access to the fractured root tip so that it may be removed. This surgical procedure usually involves laying a gingival flap and removal of the cortical and cancellous bone with a surgical hand piece in order to reach the fractured root tip. Use of this surgical procedure can lead to increased post operative pain for the patient, loss of bone that could be used for reconstructive purposes and sensitivity of adjacent teeth.

From this discussion it can seen that it would be desirable to have an instrument that could be used to facilitate the removal of roots in a manner that allows the sectioned roots to be removed individually without the fracture that could necessitate surgical intervention.

SUMMARY OF THE INVENTION

It is the primary objective of the present invention to provide a dental forceps that is capable of being disassembled and used as two separate instruments during the removal of molar roots from the mandible.

It is an additional objective of the present invention to provide such a dental forceps that, when used as a whole, can effectively remove a sectioned molar root from the mandible of a patient.

It is a further objective of the present invention to provide such a dental forceps that, when used as a part of the whole, can be used to apply rotational force between the roots of the sectioned molar which helps to loosen them within the Peridontium and aids in their removal.

It is a still further objective of the present invention to provide such a dental forceps that, when used as a part of the whole, can be used to apply vertical force to the roots of a sectioned molar which also helps to loosen them within the Peridontium and aids in their removal.

Finally, it is the objective of the present invention to provide a dental forceps that will lessen the invasive nature of sectioned molar removal which will result in less post-operative pain to the patient.

These objectives are accomplished by the use of a dental forceps that is made of surgical stainless steel, titanium alloy, or other such material that is appropriate for the construction of such instruments. The dental forceps are primarily made up of a pair of parallel handles that are pivotally mounted to one another towards their forward ends. This pivotal attachment allows the rearward portion of the handles to be manipulated towards and away from each other around the pivot point which in turn opens and closes the forceps jaws that are located on the invention forward of the pivot point.

The two jaws of the invention are each ninety degree extensions of the handles, the most forward jaw being part of the lower handle and the rearward jaw being part of the upper handle.

Each of the jaw components are constructed in a manner so that they taper to a relatively flat point when looking down the length of the invention and they taper to a very fine point when looking at the invention from the side. Additionally, the inner surface of the jaws is constructed in a slightly concave manner which aids in grasping irregularly shaped objects such as molar roots.

The design of the jaws of the present invention allows the operator to grip the mesial and distal surfaces of the root during the extraction process which provides more gripping surface area than the previous method of gripping on the buccal lingual surfaces of the root. This feature decreases slipping of the instrument from the root surface and allows for the easier removal of the roots of a sectioned molar then was previously available. Thus, the jaws of the present invention are designed in a manner that will allow them to securely grasp and remove irregularly shaped objects from small and relatively inaccessible places such as the mandible of a dental patient and to do so in a manner that will result in less trauma and post-operative pain to the patient.

Additionally, the individual handles of the present invention can also be used as separate dental instruments when the forceps is disassembled. The disassembly is accomplished by removing a screw at the pivot point and separating the lower and upper handles. The lower handle is then configured as a handle with a ninety degree downwardly oriented spike having a curved outer edge and a straight inward edge. Additionally, the upper surface of the lower handle that is located directly over the jaw is equipped with a ridged grip surface that provides a point at which leverage can be applied to the front portion of the instrument during its use.

In the disassembled configuration, the present invention is used in two fashions to apply rotational and upward force to the mesial and distal roots of mandibular molars after they have been sectioned. The first of these is to place the tip of the jaw of the instrument between the mesial and distal roots and to rotate the handle of the invention in a clockwise and counter clockwise manner. The second manner in which the disassembled invention is used is to place the tip of the jaw against the mesial and distal surfaces of the roots themselves and again to apply clockwise and counter clockwise rotational force to the molar roots. The rotational forces applied in this manner is transferred to the mesial and distal roots by the tip of the jaw and serves to help loosen the roots from the socket prior to their removal which makes their extraction much easier and lessens the resulting trauma and post-operative pain to the patient.

For a better understanding of the present invention reference should be made to the drawings and the description in which there are illustrated and described preferred embodiments of the present invention.

DESCRIPTION OF THE DRAWINGS

FIG. 4 is a side elevation view of the lower handle and jaw of FIG. 1 and illustrates the configuration of the present invention as it is used in its disassembled configuration.

FIG. 5 is a front elevation view of the invention of FIG. 1 illustrating the relative width of the jaws in relation to the body of the invention.

FIG. 6 is an enlarged cross sectional view of the invention's jaws of FIG. 5 and taken along lines 3—3 and illustrates the construction of the interior surfaces of the jaws.

FIG. 7 is a top elevation cross sectional view of one of the jaws of FIG. 6 and illustrates the manner in which the disassembled invention is used to apply rotational force to the mesial and distal roots of a sectioned molar.

FIG. 8 is a side elevation view of the forward portion of the invention of FIG. 4 and illustrates the manner in which it is used to apply rotational force to the individual mesial and distal roots.

DESCRIPTION OF THE PREFERRED EMBODIMENT

Figure 1:
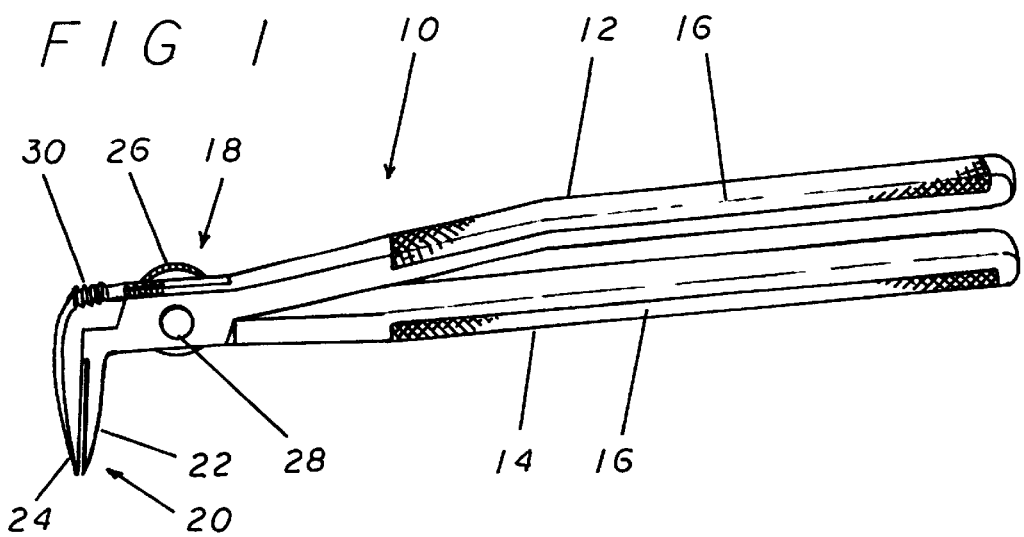
FIG. 1 is a perspective view of the present invention illustrating the orientation of the forceps jaws in relation to the upper and lower handles.
Figure 2:
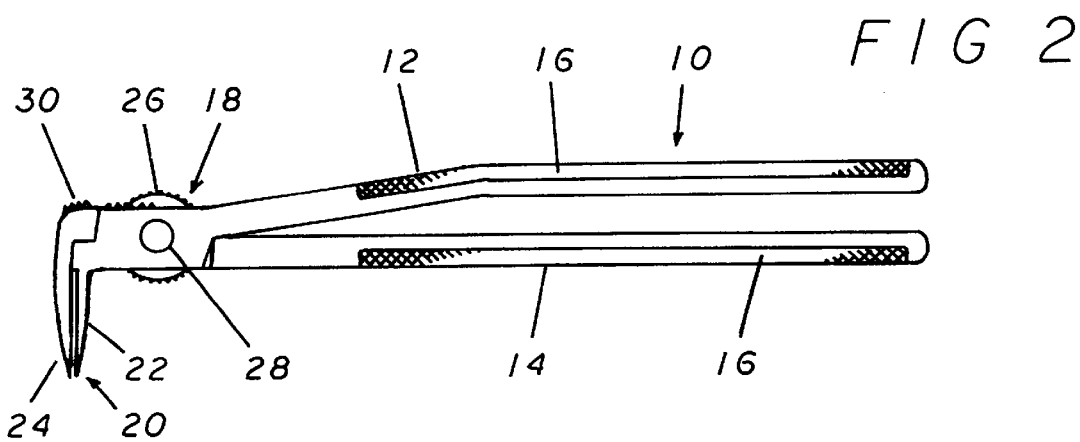
FIG. 2 is a side elevation view of the invention of FIG. 1 and shows the orientation of the forceps jaws in relation to the upper and lower handles.
Figure 3:
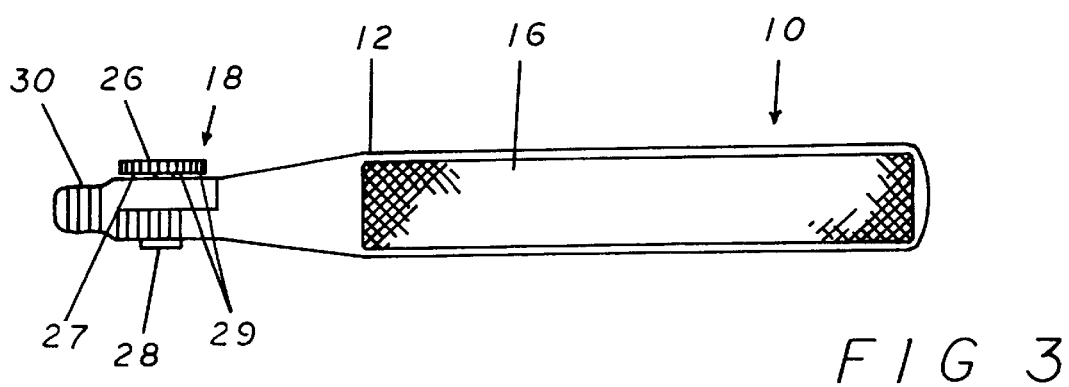
FIG. 3 is a top elevation view of the invention of FIG. 1 and shows the orientation of the forceps jaws in relation to the upper and lower handles detailing.

Referring now to the drawings, and more specifically to FIGS. 1, 2, and 3, the breakdown dental forceps 10 is essentially a dental pliers that is made of surgical stainless steel, titanium alloy, or other suitable material that is commonly used for the construction of similar precision instruments. The use of these materials for the construction of such instruments is critical because they are precision in nature and therefore require fine machining and they must be sterilized after each use and are thus very often exposed to extreme changes in temperature during the sterilization process.

The breakdown dental forceps 10 is primarily made up of an upper handle 12 and a lower handle 14 that extends parallel to each other and which are connected to each other towards their forward end at the pivot joint 18. The pivot joint 18 allows the upper and lower handles, 12 and 14, to be manipulated towards and away from each other which allows the jaws 20 of the invention to be opened and closed as needed by the function being performed. Additionally, both the upper and lower handles, 12 and 14, have on their upper and lower surfaces, respectively, a handle grip surface 16 which provide the operator with a non-slip surface for precise control over the present invention during dental procedures.

The pivot joint 18 also functions to hold the upper and lower handles, 12 and 14, together when the invention is in the assembled configuration. The pivot joint 18 is fashioned at the forward end of the upper and lower handles, 12 and 14, by changing the orientation of the upper and lower handles, 12 and 14, from running parallel to one another in the horizontal plane to running parallel to one another in the vertical plane. These vertically parallel surfaces are highly machined in the construction of the invention and are then pivotally joined together by the use of the joint screw 26 which passes through the upper and lower handles, 12 and 14, at the pivot joint 18 and which is secured in that position by threading into the screw cap 28 which is located on the opposite side of the pivot joint 18 to the point of ingress of the joint screw 26. This method of construction allows the upper and lower handles, 12 and 14, to be manipulated towards and away from one another which in turn opens and closes the invention's jaw apparatus 20 which is located forward of the pivot joint 18.

The jaw apparatus 20 of the present invention are made up of the outer and inner jaws, 22 and 24, which are ninety degree downwardly angled extensions of the lower and upper handles, 14 and 12, respectively. Both the outer and inner jaws, 22 and 24, taper inward from their point of deflection from their respective handle to form a flattened jaw point 44 at their terminal end. The function of the flattened jaw point 44 is to allow the jaw apparatus 20 to reach into narrow spaces and firmly grasp and retract objects that are contained therein. Additionally, the inner facing surfaces of both the outer and inner jaws, 22 and 24, are constructed in a manner so that they form a concave jaw gripping surface 46 (the construction of which is illustrated in FIG. 6) with respect to the body of the outer and inner jaws, 22 and 24, individually. This method of construction of the outer and inner jaws, 22 and 24, allows the jaw apparatus 20 to effectively grasp and retract irregularly shaped objects such as molar roots.

The construction of the pivot joint 18 and the joint screw 26 are best illustrated in FIGS. 3, 4, and 5, which show the position of the joint screw 26 in relation to the pivot joint 18 and the body of the invention. The joint screw 26 facilitates another important feature of the pivot joint 18 of the present invention which is that it allows the upper and lower handles, 12 and 14, to be separated from one another. This ability to separate the lower handle 14 from the upper 12 is important not only for the purposes of cleaning the invention, but also the separation of the handles allows the lower handle 14 to be used as a separate dental instrument.

The disassembly and assembly processes of the present invention are facilitated by the design of the joint screw 26 which has a relatively large screw wheel 27 which is the component of the joint screw 26 upon which rotational force is applied to install and remove it from the screw cap 28 after it passes through the screw hole 42 located in adjoining spots of the pivot joint 18 area of the upper and lower handles, 12 and 14. The screw wheel 27 is equipped with a plurality of wheel ridges 29 on its outer most surface which allows the operator to easily grip and rotate the screw wheel 27 during the assembly and disassembly of the invention. Therefore, the operator can easily remove the joint screw 26 from the pivot joint to disassemble the invention which allows him to use the lower handle 14, and its associated outer jaw 24 as a separate instrument.

The configuration of the lower handle 14 as a separate dental instrument is illustrated in FIG. 4. In this configuration, the lower handle 14 and its associated outer jaw 24 are used as a sort of dental elevator in which the jaw point 44 of the outer jaw 24 is placed in a specific area and force is applied to the lower handle 14 by the operator. The application of force on the lower handle 14 is aided by both the gripping surface 16 located on its lower surface and by the thumb grip 30 located on its upper surface just above the outer jaw 24. Thus, force is applied to the lower handle 14 by the operator grasping the gripping surface 16 between the fingers and palm and then placing the fore finger from the same hand on top of the thumb grip 30. This allows the operator to rotate the rearward portion of the lower handle 14 in a clockwise and counter clockwise manner which in turn directs that force to the object upon which the jaw point 44 is placed, further, this allows the hand inside of the patients mouth during the procedure.

The manner in which the lower handle 14 is used as a separate dental instrument is illustrated in FIGS. 7 and 8. These FIGS. depict a small section of a typical mandible including the gingiva 34, two intact molars 32, and a sectioned molar 33. A sectioned molar 33 is a damaged molar 32 that has had the upper portion of it divided so that its root 36 can be more easily extracted from the mandible 34. The typical orientation of the molar roots 36, including the mesial and distal roots, 38 and 40, of the sectioned molar 33 are further detailed in FIG. 8 which further illustrates the orientation of the mesial and distal roots, 38 and 40, in relation to the roots 36 of the healthy molars 32 in the Peridontium 34.

As a separate tool, the lower handle 14 and outer jaw 22 are used in basically two different manners. The first of these is detailed in FIG. 7 and is accomplished by placing the jaw point 44 of the outer jaw 24 in the space between the mesial and distal roots, 38 and 40, and rotating the lower handle 14 in a clockwise and counter clockwise manner. This rotating motion places of either handle places outward pressure on the mesial and distal roots, 38 and 40, which helps to loosen them within the socket 34 which makes the later extraction with the jaw apparatus 20 of the present invention significantly easier.

An additional use of the lower handle 14 and outer jaw 22 as a separate dental instrument is illustrated in FIG. 8, the upper handle may also be used as a similar instrument (NOT SHOWN IN FIG. 8). With this use, the jaw point 44 is employed to loosen an individual section of root 36 by placing the jaw point 44 against the outside surface of the root 36 section and again applying rotational force to it in much the same manner as described above. This rotational motion on both the mesial and distal root surfaces again functions to loosen the root 36 section which makes it easier to extract.

Although the present invention has been described in considerable detail with reference to certain preferred versions thereof, other versions are possible. Therefore, the spirit and scope of the appended claims should not be limited to the description of the preferred versions contained herein.

What is claimed is:

1. A dental forceps having a upper and lower pivotally connected member said members formed at one end to provide handles and at the other end to provide gripping jaws, said dental forceps further comprising;
   a first jaw extending substantially perpendicular to said upper member so as to form an L shaped upper member wherein said first jaw and said upper member are in substantially the same first plane;
   a second jaw extending substantially perpendicular to said lower member so as to form an L shaped lower member wherein said second jaw and said lower member are in substantially the same second plane;
   a removable fastener for connecting said upper and lower members at a pivot point such that said upper and lower members may pivot about said fastener and said first plane and said second plane become the same plane; and
   a cap on said fastener so that said fastener may be removed from said upper and lower member without the use of tools.

2. A dental forceps as in claim 1 wherein said lower member further comprises an elongate handle section that is substantially straight and perpendicular to said second jaw.

3. A dental forceps as in claim 2 wherein said second jaw further comprises a tapered section which has an inner concave surface facing said elongate handle section.

4. A dental forceps as in claim 3 wherein said lower member further comprises a ridged grip section directly above said second jaw.

5. A dental forceps as in claim 4 wherein said upper member further comprises a curved elongate handle section and said first jaw has a tapered section which has an outer concave surface facing away from said elongate handle section.

6. A dental forceps as in claim 5 wherein said upper member further comprises a ridged grip section above said pivot point.

7. A dental forceps comprising:
   an upper member having an elongate handle section;
   a lower member having an elongate handle section;
   a first jaw extending substantially perpendicular to said upper member so as to form an L shaped upper member wherein said first jaw and said upper member are in substantially the same first plane;
   a second jaw extending substantially perpendicular to said lower member so as to form an L shaped lower member wherein said second jaw and said lower member are in substantially the same second plane;
   a removable fastener for connecting said upper and lower member at a pivot point such that said upper and lower members may pivot about said fastener and said first plane and said second plane become the same plane; and
   a means of removing said fastener without the use of special tools.

8. A dental forceps as in claim 7 wherein said means of removing said fastener is thumb wheel which may be turned by hand.

9. A dental forceps as in claim 8 wherein said lower members elongate handle section is substantially straight and perpendicular to said second jaw.

10. A dental forceps as in claim 9 wherein said second jaw further comprises a tapered section which has an inner concave surface facing said elongate handle section.

11. A dental forceps as in claim 10 wherein said upper members elongate handle section is angled.

12. A dental forceps as in claim 11 wherein said first jaw further comprises a tapered section which has an outer concave surface facing away from said elongate handle section.

13. A dental forceps as in claim 11 wherein said lower member further comprises a ridged grip section above said second jaw.

14. A dental forceps comprising:
   an upper member having a angled elongate handle section;
   a lower member having a straight elongate handle section;
   a first jaw extending substantially perpendicular to said upper member so as to form an L shaped upper member wherein said first jaw and said upper member are in substantially the same first plane, said jaw having a concave surface facing away from said elongate handle section;
   a second jaw extending substantially perpendicular to said lower member so as to form an L shaped lower member wherein said second jaw and said lower member are in substantially the same second plane, said jaw having a concave surface facing towards said elongate handle section so as to form a cavity section between said first and second jaw; and
   a pivot point such that said upper and lower members may pivot about said point and said first plane and said second plane become the same plane.

15. A dental forceps as in claim 14 further comprising a removable fastener for pivotally connecting said upper and lower member at said pivot point.

16. A dental forceps as in claim 15 wherein said fastener further comprising a thumb wheel may be turned by hand for removal of said fastener.

17. A dental forceps as in claim 16 wherein said jaws taper inward away from said elongate handle sections.

18. A dental forceps as in claim 17 wherein said lower member further comprises a ridged grip section above said second jaw.

* * * * *